United States Patent
Farrand et al.

(10) Patent No.: US 7,034,174 B2
(45) Date of Patent: *Apr. 25, 2006

(54) MONO-, OLIGO- AND POLYMERS COMPRISING A 2,6-AZULENE GROUP AND THEIR USE AS CHARGE TRANSPORT MATERIALS

(75) Inventors: Louise Diane Farrand, Spetisbury, Blandford Forum (GB); Michael Findlater, Glasgow (GB); Mark Giles, Southampton (GB); Martin Heeney, Southampton (GB); Steven Tierney, Southampton (GB); Marcus Thompson, Fordingbridge (GB); Maxim Shkunov, Southampton (GB); David Sparrowe, Southbourne (GB); Iain McCulloch, Kings Somborne (GB)

(73) Assignee: MERCK Patent GmbH, Darmstadt (DE)

( * ) Notice: Subject to any disclaimer, the term of this patent is extended or adjusted under 35 U.S.C. 154(b) by 195 days.

This patent is subject to a terminal disclaimer.

(21) Appl. No.: 10/314,939

(22) Filed: Dec. 10, 2002

(65) Prior Publication Data
US 2003/0122479 A1    Jul. 3, 2003

(30) Foreign Application Priority Data
Dec. 10, 2001 (EP) .................................. 01129216

(51) Int. Cl.
*C07F 7/02* (2006.01)

(52) U.S. Cl. ...................... 556/400; 558/248; 558/265; 564/439; 569/76; 568/38; 568/632

(58) Field of Classification Search ................ 313/504; 556/400; 558/248, 265; 560/76; 564/439; 568/38, 632; 428/690; 569/76
See application file for complete search history.

(56) References Cited

U.S. PATENT DOCUMENTS

| | | | |
|---|---|---|---|
| 4,738,908 | A | 4/1988 | Oguchi et al. |
| 5,037,575 | A | 8/1991 | Miura et al. |
| 5,198,153 | A | 3/1993 | Angelopoulos et al. |
| 5,892,244 | A | 4/1999 | Tanaka et al. |
| 5,998,805 | A | 12/1999 | Suh et al. |
| 6,136,225 | A | 10/2000 | Meyer et al. |
| 2004/0164272 | A1 | 8/2004 | Buchecker et al. |

FOREIGN PATENT DOCUMENTS

| | | |
|---|---|---|
| DE | 34 25 511 | 1/1986 |
| DE | 39 29 383 | 3/1991 |
| DE | 39 38 094 | 5/1991 |
| DE | 44 45 619 | 6/1996 |
| EP | 0 187 015 | 7/1986 |
| EP | 0 187 015 A2 * | 7/1986 |
| EP | 0 528 662 | 2/1993 |
| EP | 0 528 662 A1 * | 2/1993 |
| EP | 1 256 602 | 11/2002 |
| WO | 96/21659 | 7/1996 |
| WO | WO 97 00600 | 1/1997 |
| WO | 00/79617 | 12/2000 |

OTHER PUBLICATIONS

Balschukat et al., Novel 2, 6-Disubstituted azulenes, Chemische Berichte (1986), 119 (7), 2272-2288.*
Kato et al., Synthesis of anti-[2,2] (2,6) Azulenophane from 5-methyltropolone, Tetrahedron Letters (1976), (24), 2045-2048.*
Keehn et al., Cyclophanes V. Anti-[2.2] (2,6) Azulenophane, Tetrehedron Letters No. 14. pp. 1043-4046, 1976.*
Daub et al., Azulene Appended Cellulose: Synthesis, Optional and Chiroptical Properties, Film Formation by Electrochemical Oxidation, Macromol. Chem. Phys. 2000, 201, 2091-2100.*
European International Search Report dated Mar. 10, 2003.
Patent Abstract of Japan No. 02-069441 dated Mar. 8, 1990.
Patent Abstract of Japan No. 02-069437 dated May 29, 1990.
Patent Abstract of Japan No. 03-122189 dated May 24, 1991.
Patent Abstract of Japan No. 02-069439 dated Mar. 8, 1990.
Patent Abstract of Japan No. 02-069438 dated Mar. 8, 1990.
Patent Abstract of Japan No. 60-104180 dated Jun. 8, 1985.
S.E. Estdale et al., "The Azulene Ring as a 1-10 Structural Element in Liquid Crystals", Journal of Materials Chemistry, vol. 7, No. 3, (1997), pp. 391-401.

* cited by examiner

*Primary Examiner*—Johann Richter
*Assistant Examiner*—Chukwuma Nwaonicha
(74) *Attorney, Agent, or Firm*—Millen White Zelano & Branigan, P.C.

(57) ABSTRACT

Conjugated mono-, oligo- and polyazulenes are suitable for use as semiconductors or charge transport materials in optical, electrooptical or electronic devices including field effect transistors, electroluminescent, photovoltaic and sensor devices, and as field effect transistors and semi-conducting components.

14 Claims, No Drawings

MONO-, OLIGO- AND POLYMERS COMPRISING A 2,6-AZULENE GROUP AND THEIR USE AS CHARGE TRANSPORT MATERIALS

FIELD OF INVENTION

The invention relates to new conjugated mono-, oligo- and polyazulenes. The invention further relates to their use as semiconductors or charge transport materials in optical, electrooptical or electronic devices including field effect transistors, electroluminescent, photovoltaic and sensor devices. The invention further relates to field effect transistors and semi-conducting components comprising the new mono-, oligo- and polyazulenes.

BACKGROUND AND PRIOR ART

Organic materials have recently shown promise as the active layer in organic based thin film transistors and organic field effect transistors [see H. E. Katz, Z. Bao and S. L. Gilat, Acc. Chem. Res., 2001, 34, 5, 359]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semi-conducting material and the current on/off ratio, so the ideal semi-conductor should have a low conductivity in the off state, combined with a high charge carrier mobility ($>1 \times 10^{-3}$ cm$^2$ V$^{-1}$ s$^{-1}$). In addition, it is important that the semi-conducting material is relatively stable to oxidation, i.e., it has a high ionisation potential, as oxidation leads to reduced device performance.

A known compound which has been shown to be an effective p-type semiconductor for OFETs is pentacene [see S. F. Nelson, Y. Y. Lin, D. J. Gundlach and T. N. Jackson, Appl. Phys. Lett., 1998, 72, 1854]. When deposited as a thin film by vacuum deposition, it was shown to have carrier mobilities in excess of 1 cm$^2$ V$^{-1}$ s$^{-1}$ with very high current on/off ratios greater than $10^6$. However, vacuum deposition is an expensive processing technique that is unsuitable for the fabrication of large-area films.

It is an aim of the present invention to provide new materials for use as semiconductors or charge transport materials, which are easy to synthesise, have high charge mobility, good processability and improved oxidative stability. Other aims of the invention are immediately evident to those skilled in the art from the following description.

The inventors have found that these aims can be achieved by providing new monomers, oligomers and polymers based on azulene.

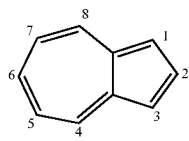

Azulene is a non-benzenoid aromatic hydrocarbon which is planar and thermodynamically stable. Polymerisation at the 2- or 6-position results in a linear structure. As a result, polyazulenes pack closely, thus exhibiting a higher degree of order that leads to particularly high charge carrier mobility.

Furthermore, by adding alkyl chains and other substituent groups to the azulene core, the azulenes can be made more soluble thus being suitable for spin coating or solution coating techniques, rather than vacuum deposition, to prepare thin films for use, e.g., in electronic devices such as transistors.

1,3-Polyazulenes (A) have been prepared electrochemically, as reported by K. Iwasaki et al, Synth. Metals, 1995, 69, 543 and Y-B. Shim et al, J. Electrochem. Soc., 1997, 144, 3027 and M. Porsch et al in Adv. Mater., 1997, 9, 635, and by stirring in strong acid, as reported by N. Kihara et al, J. Amer. Chem. Soc., 1997, 30, 6385. Azulene appended cellulose has also been reported [see F. X. Redl et al, Macromol. Chem. Phys., 2000, 201, 2091]

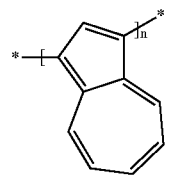

A

Copolymers of azulene have also been reported. DE 34 25 511, DE 3929383 and DE 39 38 094 disclose a copolymerisate of pyrrole and azulene obtained by electrochemical polymerisation in the presence of sulfonic acid and a conducting salt. DE 44 45 619 discloses a copolymer with azulene and phenylene units linked by phenylmethylene groups.

However, polyazulenes polymerised at the 2- and 6-position according to the present invention have not been reported.

Another aspect of the present inventions relates to advantageous uses of the mono-, oligo- and polyazulenes, including their oxidatively or reductively doped forms, according to the invention.

DEFINITION OF TERMS

The term 'film' includes self-supporting, i.e., free-standing, films that show more or less pronounced mechanical stability and flexibility, as well as coatings or layers on a supporting substrate or between two substrates.

SUMMARY OF THE INVENTION

One object of the invention is to provide mono-, oligo- and polymers comprising at least two azulene-2,6-diyl groups.

Another object of the invention is the use of mono-, oligo- and polyazulenes according to the invention as semiconductors or charge transport materials, in particular in optical, electrooptical or electronic devices, like, for example, components of integrated circuitry, field effect transistors (FET), for example, as thin film transistors in flat panel display applications or for Radio Frequency Identification (RFID) tags, or in semiconducting components for organic light emitting diode (OLED) applications such as electroluminescent displays or backlights of, e.g., liquid crystal displays, for photovoltaic or sensor devices, as electrode materials in batteries, as photoconductors and for electrophotographic applications like electrophotographic recording.

Another object of the invention is to provide a field effect transistor, for example, as a component of integrated circuitry, as a thin film transistor in flat panel display applications, or in a Radio Frequency Identification (RFID) tag, comprising one or more mono-, oligo- or polyazulenes according to the invention.

Another object of the invention is to provide a semiconducting component, for example in OLED applications like electroluminescent displays or backlights of, e.g., liquid crystal displays, in photovoltaic or sensor devices, as electrode materials in batteries, as photoconductors and for electrophotographic applications, comprising one or more mono-, oligo- or polymers according to the invention.

Another object of the invention is to provide a security marking or device comprising an RFID or ID tag or a FET according to the invention.

Upon further study of the specification and appended claims, further objects and advantages of this invention will become apparent to those skilled in the art.

DETAILED DESCRIPTION OF THE INVENTION

The mono-, oligo- and polyazulenes according to the present invention are especially useful as charge transport semiconductors in that they have high carrier mobilities. Particularly preferred are mono-, oligo- and polyazulenes wherein the azulene group is substituted by one or more alkyl or fluoroalkyl groups. The introduction of alkyl side chains to the azulene group and attached rings improves the solubility and therefore the solution processibility of the inventive materials.

Especially preferred are mono-, oligo- and polymers comprising one or more identical or different recurring units of formula I

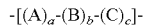   I wherein
  A and C are independently of each other and independently in each occurrence —CX$^1$═CX$^2$—, —C≡C—, or optionally substituted arylene or heteroarylene, or have one of the meanings of B,
  X$^1$ and X$^2$ are independently of each other H, F, Cl or CN,
  B is independently in each occurrence azulene-2,6-diyl, [2,6']-bisazulene-6,2'-diyl, [2,2']-bisazulene-6,6'-diyl, [6,6']-bisazulene-2,2'-diyl, all of which are substituted or unsubstituted, or a mirror image of one of these groups, and
  a, b and c are independently of each other 0, 1, 2 or 3, e.g., 0, 1 or 2, with a+b+c>0, with the proviso that the mono-, oligo- and polyazulenes comprise at least two azulene-2,6-diyl groups or at least one [2,6']-bisazulene-6,2'-diyl, [2,2']-bisazulene-6,6'-diyl or [6,6']-bisazulene-2,2'-diyl group.

In the oligo- and polymers of the present invention the recurring units (A)$_a$-(B)$_b$-(C)$_c$ in case of multiple occurrence can be selected of formula I independently of each other, so that an oligo- or polymer may comprise identical or different recurring units (A)$_a$-(B)$_b$-(C)$_c$. The oligo- and polymers thus include homopolymers and copolymers like for example
  statistically random copolymers, for example with a monomer sequence such as -A-B-C-C-B-A-B-,
  alternating copolymers, for example with a monomer sequence such as -A-B-C-A-B-C-, and
  block copolymers, for example with a monomer sequence such as -A-A-B-B-B-B-C-C-C-, wherein the groups A and C preferably form a conjugated system together with the group B.

Further preferred are mono-, oligo- and polymers comprising one or more recurring units (A)$_a$-(B)$_b$-(C)$_c$, wherein a=c=0 and b=1, very preferably consisting exclusively of such recurring units.

Further preferred are mono-, oligo- and polymers comprising one or more recurring units (A)$_a$-(B)$_b$-(C)$_c$, wherein b=c=1 and a=0, very preferably consisting exclusively of such recurring units.

Further preferred are mono-, oligo- and polymers comprising one or more recurring units (A)$_a$-(B)$_b$-(C)$_c$, wherein a=b=c=1, very preferably consisting exclusively of such recurring units.

Especially preferred are mono-, oligo- and polymers of formula I1

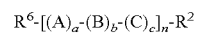   I1 wherein A, C, a, b and c are as defined in formula I,
  B is independently in each occurrence a group selected of formulae IIa to IId or their mirror images

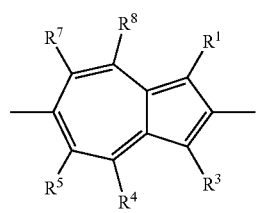   IIa

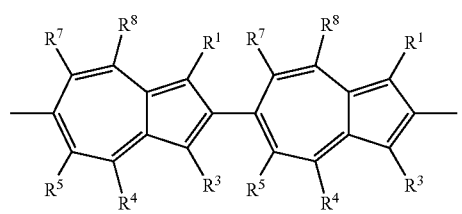   IIb

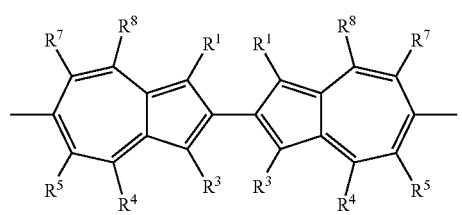   IIc

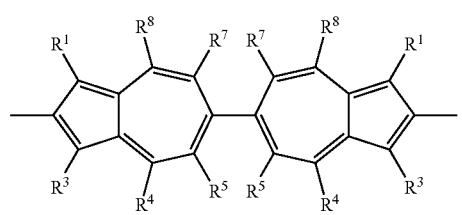   IId

R$^1$ to R$^8$ are independently of each other H, halogen or straight chain, branched or cyclic alkyl with 1 to 20 C-atoms, which is unsubstituted, mono- or poly-substituted by F, Cl, Br, I or CN, and in which one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, $R^0$ and $R^{00}$ are independently of each other H or alkyl with 1 to 12 C-atoms, n is an integer from 1 to 5000, wherein the recurring units $[(A)_a\text{-}(B)_b\text{-}(C)_c]$ can be identical or different.

Especially preferred are mono-, oligo- and polymers of formula I1 wherein n is an integer from 2 to 5000, in particular from 20 to 1000, n is an integer from 2 to 5, the molecular weight is from 5000 to 100000, $R^1$, $R^3$, $R^4$, $R^5$, $R^7$ and $R^8$ are each independently selected from H, $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, and optionally substituted aryl or heteroaryl, $R^2$ and $R^6$ are each independently selected from $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, and optionally substituted aryl or heteroaryl, A and C are each independently optionally substituted arylene or heteroarylene, A and C are each independently —$CX^1$=$CX^2$— or —C≡C—, in at least one monomer unit $(A)_a\text{-}(B)_b\text{-}(C)_c$ a, b and c are 1, and one of A and C is arylene or heteroarylene and the other is —$CX^1$=$CX^2$— or —C≡C—, n>1.

Especially preferred are mono-, oligo- and polymers of the following formulae

Ia
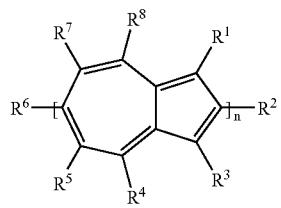

Ib
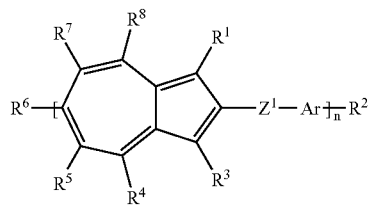

Ic
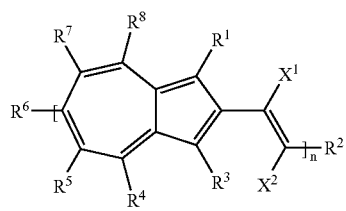

-continued

Id
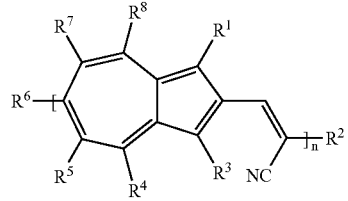

Ie
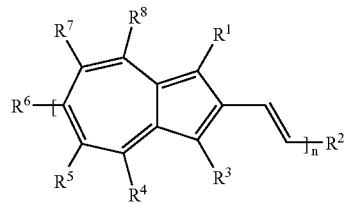

If
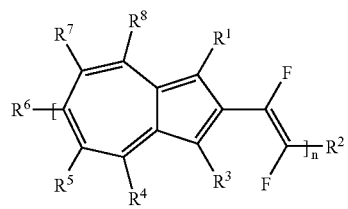

Ig
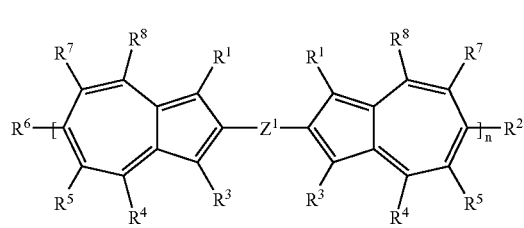

Ih
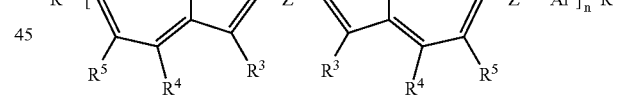

Ii
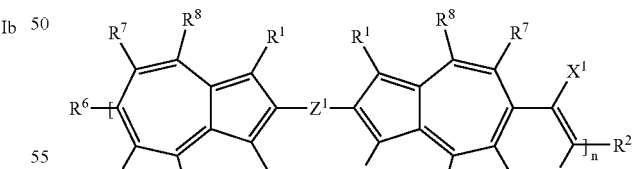

Ik
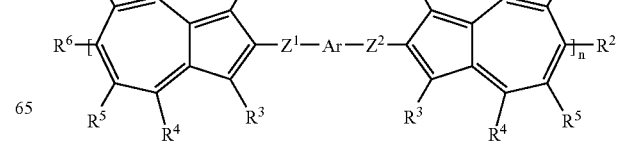

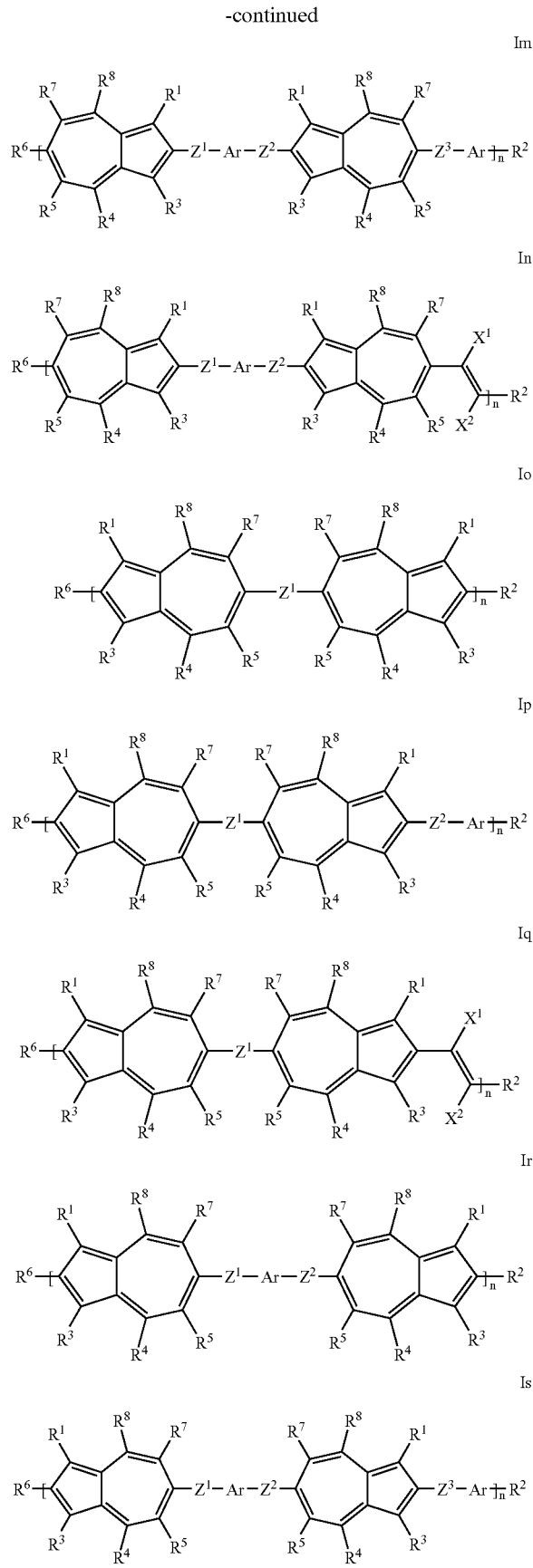
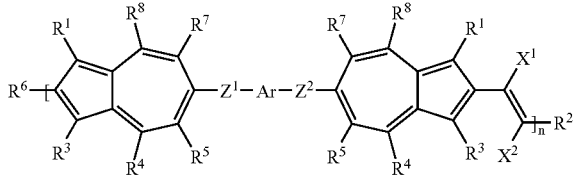

wherein $R^1$ to $R^8$ and n have the meanings given in formula I1,

Ar is $(ar)_m$, with ar being arylene or heteroarylene and m being 1, 2 or 3, $Z^1$, $Z^2$ and $Z^3$ are independently of each other —$CX^1$=$CX^2$—, —C≡C— or a single bond, and $X^1$ and $X^2$ have the meanings given in formula I.

In these preferred formulae, $R^1$, $R^3$, $R^4$, $R^5$, $R^7$ and $R^8$ are very preferably F or alkyl with 1 to 16 C-atoms that is optionally fluorinated, $R^2$ and $R^6$ are very preferably H, halogen or alkyl with 1–16 C atoms that is optionally fluorinated, ar is very preferably 1,4-phenylene, alkoxyphenylene, alkylfluorene, thiophene-2,5-diyl, thienothiophene-2,5-diyl or dithienothiophene-2,6-diyl, m is preferably 1, n is preferably an integer from 2 to 5000, in particular from 20 to 1000.

In the formulae shown above and below, aryl and heteroaryl preferably denote a mono-, bi- or tricyclic aromatic or heteroaromatic group with up to 25 C atoms that optionally comprises fused rings and is optionally substituted with one or more groups selected from H, halogen and straight chain, branched or cyclic alkyl with 1 to 20 C-atoms, which is unsubstituted, mono- or poly-substituted by F, Cl, Br, I or CN, and in which one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another.

Especially preferred aryl and heteroaryl groups are phenyl in which, in addition, one or more CH groups are optionally replaced by N, naphthalene, thiophene, thienothiophene, dithienothiophene, alkyl fluorene and oxazole, all of which are unsubstituted, mono- or polysubstituted with L, wherein L is halogen or an alkyl, alkoxy, alkylcarbonyl or alkoxycarbonyl group with 1 to 12 C atoms, wherein one or more H atoms are optionally replaced by F or Cl.

Arylene and heteroarylene preferably denote a bivalent mono-, bi- or tricyclic aromatic or heteroaromatic group with up to 25 C atoms that optionally comprises fused rings and is optionally substituted with one or more groups selected from H, halogen and straight chain, branched or cyclic alkyl with 1 to 20 C-atoms, which is unsubstituted, mono- or poly-substituted by F, Cl, Br, I or CN, and in which one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another.

Especially preferred arylene and heteroarylene groups are 1,4-phenylene in which, in addition, one or more CH groups are optionally replaced by N, naphthalene-2,6-diyl, thiophene-2,5-diyl, thienothiophene-2,5-diyl, dithienothiophene-2,6-diyl, alkyl fluorene and oxazole, all of which are unsubstituted, mono- or polysubstituted with L as defined above.

Further preferred aryl and heteroaryl groups include five-membered heterocyclics like oxazole or isoxazole, N-substituted imidazole or pyrazole, thiazole or isothiazole, oxadiazole, N-substituted triazole, six-membered heterocyclics like pyridine, pyridazine, pyrimidine, pyrazine, triazine and tetrazine, heterocyclics with fused rings like benzoxazole, benzothiazole, benzimidazole, quinoline, isoquinoline, cinnoline, quinazoline, quinoxaline, phthalazine, benzothiadiazole, benzotriazole, benzotriazine, phenazine, phenanthridine, acridine, or condensed polycyclics like acenaphthene, phenanthrene, anthracene, fluoranthene, pyrene, perylene, rubrene, chrysene, naphthacene, coronene or triphenylene, all of which are unsubstituted, mono- or polysubstituted with L as defined above.

$CX^1=CX^2$ is preferably —CH=CH—, —CH=CF—, —CF=CH—, —CF=CF—, —CH=C(CN)— or —C(CN)=CH—.

If in the formulae shown above and below, one of $R^1$ to $R^8$ is an alkyl or alkoxy radical, i.e., where the terminal $CH_2$ group is replaced by —O—, this may be straight-chain or branched. It is preferably straight-chain, has 2 to 8 carbon atoms and accordingly is preferably ethyl, propyl, butyl, pentyl, hexyl, heptyl, octyl, ethoxy, propoxy, butoxy, pentoxy, hexyloxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e., where one $CH_2$ group is replaced by —O—, is preferably straight-chain 2-oxapropyl(=methoxymethyl), 2-(=ethoxymethyl) or 3-oxabutyl(=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

"Fluorinated alkyl" or "fluoroalkyl" is mono-, poly- or perfluorinated alkyl, preferably $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$.

Halogen is preferably F or Cl.

The mono-, oligo- and polyazulenes of the present invention can be synthesized according to or in analogy to known methods. Some preferred methods are described below.

As shown in Scheme 1, Ullmann-type coupling (see T. Morita and K. Takase, *Bull. Chem. Soc. Jpn.*, 1982, 55, 1144–1152) gives biazulene (1) followed by bromination (see T. Nozoe, T. Asao and M. Oda in *Bull. Chem. Soc. Jpn.*, 1974, 47, 681) gives compound (2) and decarboxylation (see D. Balschukat and E. V. Dehmlow, *Chem. Ber.*, 1986, 119, 2272) gives the 2,2'-biazulene (3). Polymerisation can proceed via conventional routes: $Ni(cod)_2$ and triphenylphosphine (Yamamoto coupling) to yield (5). Alternatively, (3) is converted to the mono-Grignard and polymerised using $Ni(dppp)Cl_2$ to yield (5). Other coupling routes are Stille coupling (see D. Milstein and J. K. Stille, *J. Am. Chem. Soc.*, 1979, 101, 4992), Rieke coupling (see T.-A. Chen and R. D. Rieke, *J. Am. Chem. Soc.*, 1992, 114, 10087), and Suzuki coupling (see N. Miyaura, T. Yanagi and A. Suzuki, *Synth. Commun.*, 1981, 11, 513).

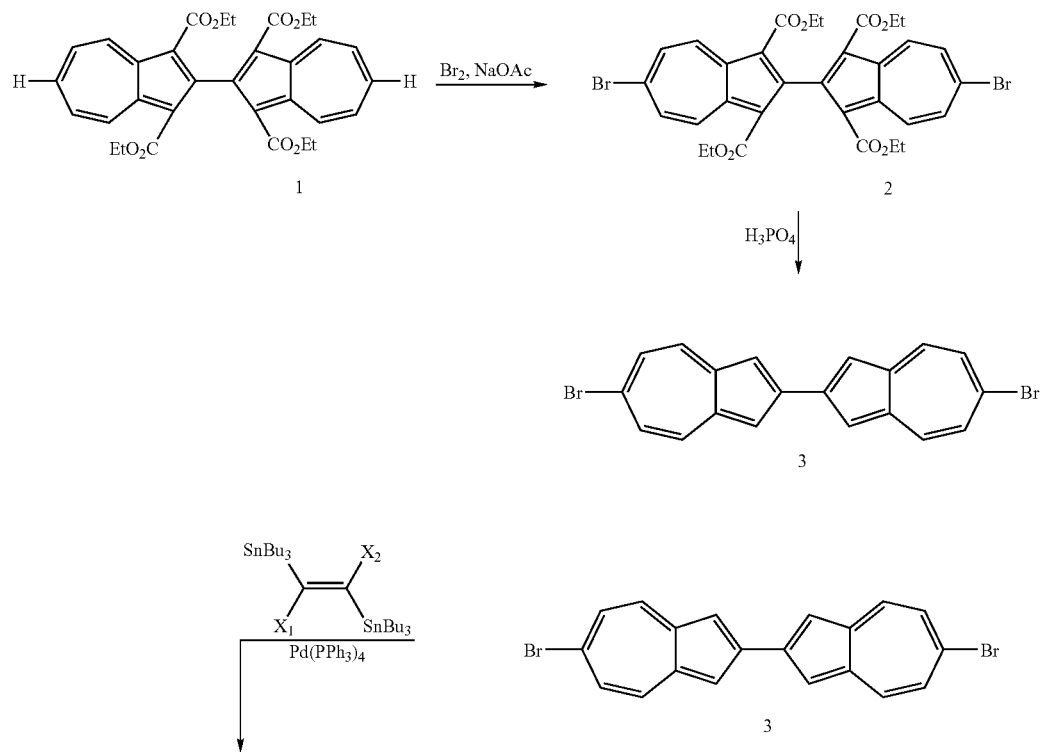

Scheme 1

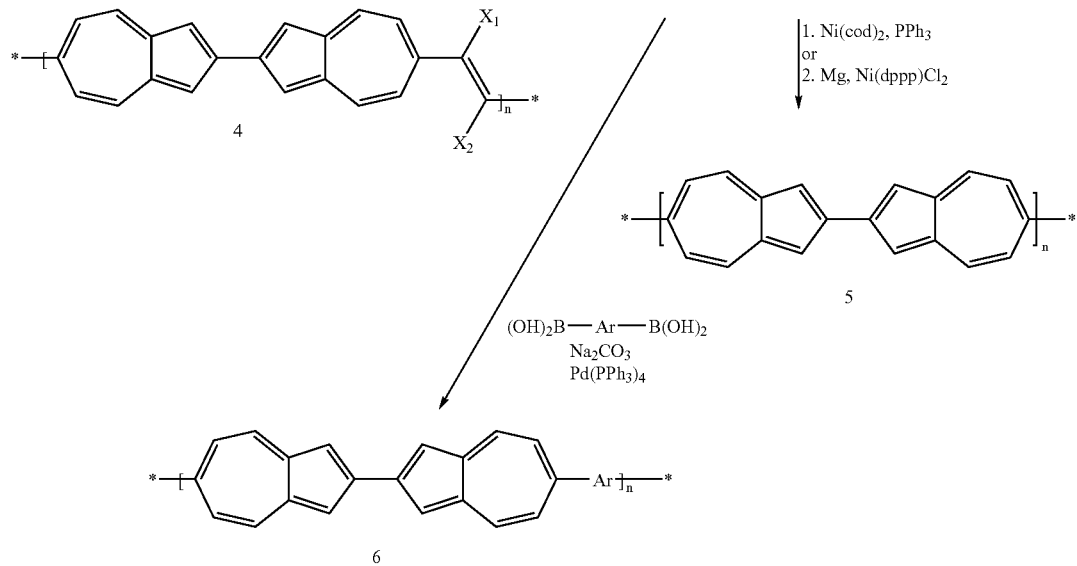

wherein Ar, $X^1$, $X^2$ and n have the meanings given in formula I and I1.

As shown in Scheme 2, (3) can be cross-coupled under Sonogashira conditions with 4-chlorophenylacetylene to give the 2,2' biazulene (8), which can be polymerised under typical and known conditions to give for example highly conjugated polymer (9).

As depicted in scheme 3, compound (10) is prepared by bromination of 2-amino-1,3-azulene diethylcarboxylate (see T. Nozoe, S. Seto and S. Matsumara, *Bull. Chem. Soc. Jpn.*, 1962, 35, 1990). (11) is the cross-coupled product of (10) with protected acetylene. The amine is converted to the chloro compound (13), decarboxylated with acid and polymerised to give (15).

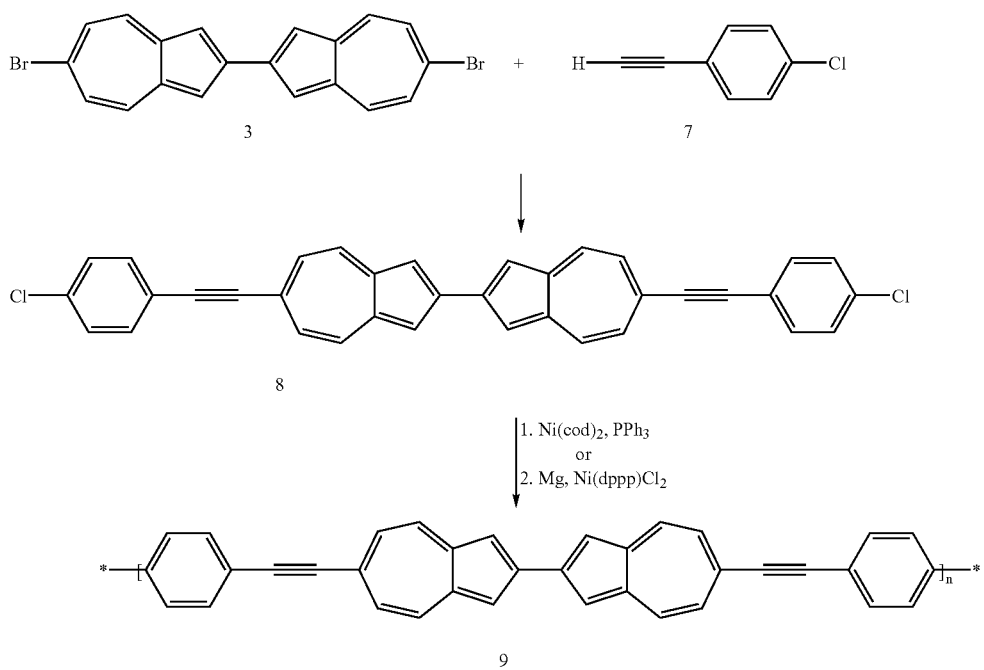

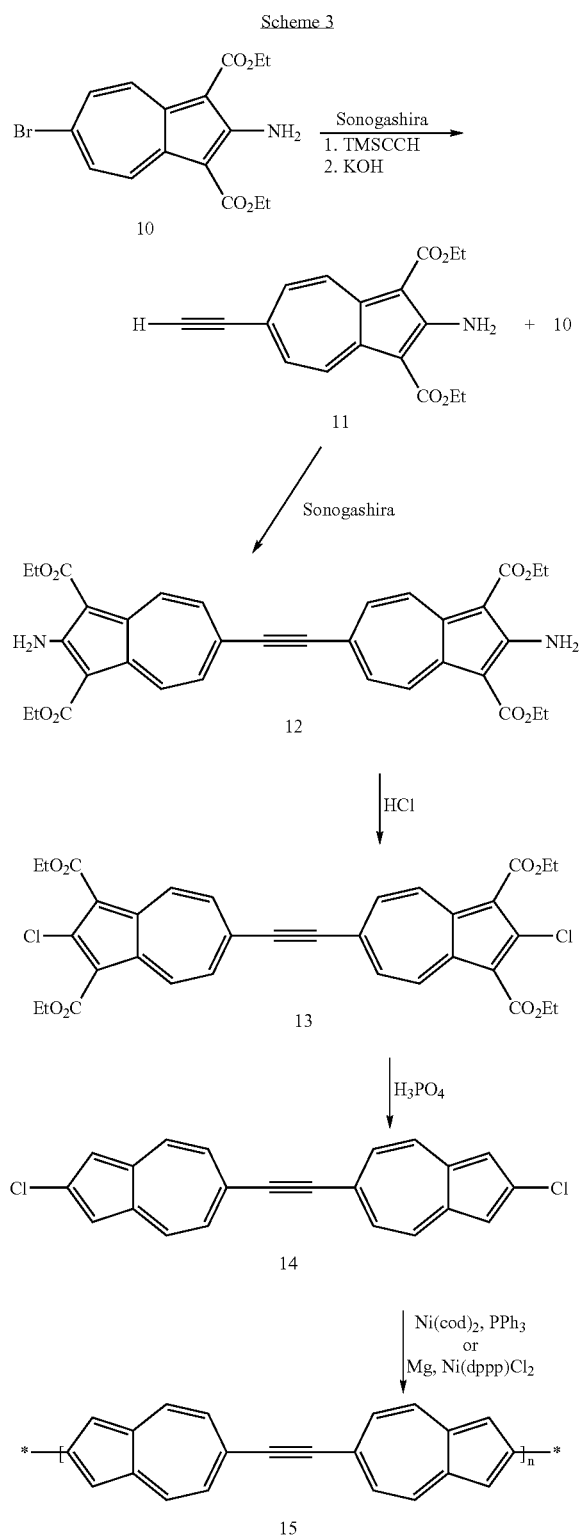

Scheme 3

A further aspect of the invention relates to both the oxidised and reduced form of the compounds and materials according to this invention. Either loss or gain of electrons results in formation of a highly delocalised ionic form, which is of high conductivity. This can occur on exposure to common dopants. Suitable dopants and methods of doping are known to those skilled in the art, e.g., from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g. $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns or tracts in electronic applications such as printed circuit boards and condensers.

The mono-, oligo- and polyazulenes of the present invention are useful as optical, electronic and semiconductor materials, in particular as charge transport materials in field effect transistors (FETs), e.g., as components of integrated circuitry, ID tags or TFT applications. Alternatively, they may be used in organic light emitting diodes (OLEDs) in electroluminescent display applications or as backlight of, e.g., liquid crystal displays, as photovoltaics or sensor materials, for electrophotographic recording, and for other semiconductor applications.

Especially the oligomers and polyazulenes according to the invention show advantageous solubility properties which allow production processes using solutions of these compounds. Thus films, including layers and coatings, may be generated by low cost production techniques, e.g., spin coating. Suitable solvents or solvent mixtures comprise alkanes and/or aromatics, especially their fluorinated derivatives.

The materials of the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semi-conductive material is arranged as a film between a gate-dielectric and a drain and a source electrode, are generally known, e.g., from U.S. Pat. No. 5,892,244, WO 00/79617, U.S. Pat. No.

5,998,804, and from the references cited in the background and prior art chapter and listed below. Due to the advantages, like low cost production using the solubility properties of the compounds according to the invention and thus the processability of large surfaces, preferred applications of these FETs are such as integrated circuitry, TFT-displays and security applications.

In security applications, field effect transistors and other devices with semi-conductive materials, like transistors or diodes, may be used for ID tags or security markings to authenticate and prevent counterfeiting of documents of value like banknotes, credit cards or ID cards, national ID documents, licenses or any product with money value, like stamps, tickets, shares, cheques etc.

Alternatively, the mono-, oligo- and polymers according to the invention may be used in organic light emitting devices or diodes (OLEDs), e.g., in display applications or as backlight of, e.g., liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, *Synthetic Materials*, 111–112, 2000, 31–34, Alcala, *J. Appl. Phys.*, 88, 2000, 7124–7128 and the literature cited therein.

According to another use, the inventive compounds, materials or films, especially those which show photoluminescent properties, may be employed as materials of light sources, e.g., of display devices such as described in EP 0 889 350 A1 or by C. Weder et al., *Science*, 279, 1998, 835–837.

The entire disclosure of all applications, patents and publications, cited above and below, and of corresponding European Patent application No. 01129216.6., filed Dec. 10, 2001 is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A mono-, oligo- or polymeric compound comprising one or more identical or different recurring units of formula I

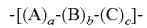

I wherein

A and C are independently of each other and independently in each occurrence —$CX^1$=$CX^2$—, —C≡C—, optionally substituted arylene, optionally substituted heteroarylene, or is substituted or unsubstituted azulene-2,6-diyl, [2,6']-bisazulene-6,2'-diyl, [2,2']-bisazulene-6,6'-diyl, [6,6']-bisazulene-2,2'-diyl, or a mirror image of one of these groups, $X^1$ and $X^2$ are independently of each other H, F, Cl or CN, B is independently in each occurrence azulene-2,6-diyl, [2,6']-bisazulene-6,2'-diyl, [2,2']-bisazulene-6,6'-diyl, [6,6']-bisazulene-2,2'-diyl, all of which are substituted or unsubstituted, or a mirror image of one of these groups, and a, b and c are independently of each other 0, 1, 2 or 3, with a+b+c>0, with the proviso that the mono-, oligo- or polymer comprises at least two azulene-2,6-diyl groups or at least one [2,6']-bisazulene-6,2'-diyl, [2,2']-bisazulene-6,6'-diyl or [6,6']-bisazulene-2,2'-diyl group.

2. A compound according to claim 1, wherein

A and C are independently of each other and independently in each occurrence —$CX^1$=$CX^2$—;

—C≡C—;

a mono-, bi- or tricyclic aromatic or heteroaromatic group with up to 25 C atoms that is optionally substituted with one or more groups selected from H, halogen and straight chain, branched or cyclic alkyl with 1 to 20 C-atoms, which is unsubstituted, mono- or poly-substituted by F, Cl, Br, I or CN, and in which one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another;

azulene-2,6-diyl or a mirror image thereof;

[2,6']-bisazulene-6,2'-diyl or a mirror image thereof;

[2,2']-bisazulene-6,6'-diyl or a mirror image thereof; or

[6,6']-bisazulene-2,2'-diyl or a mirror image thereof.

3. A compound according to claim 1, wherein said compound is selected of formula I1

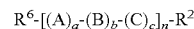

I1 wherein

B is independently in each occurrence selected from formulae IIa to IId and their mirror images

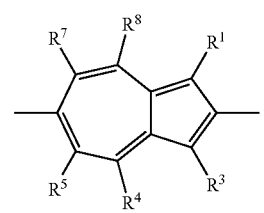

IIa

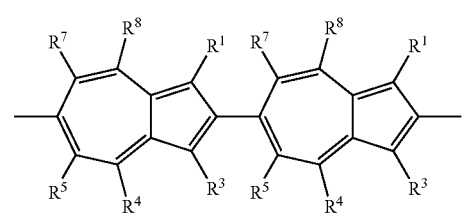

IIb

-continued

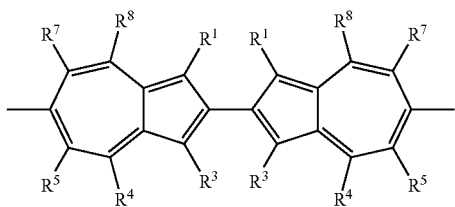
IIc

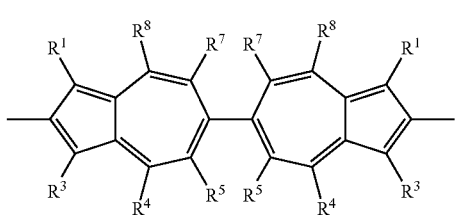
IId

R¹ to R⁸ are independently of each other H,
halogen,
straight chain, branched or cyclic alkyl with 1 to 20 C-atoms, which is unsubstituted, mono- or poly-substituted by F, Cl, Br, I or CN, and in which one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH═CH— or —C≡C— in such a manner that O and/or S atoms are not linked directly to one another,
optionally substituted aryl, or
optionally substituted heteroaryl,
R⁰ and R⁰⁰ are independently of each other H or alkyl with 1 to 12 C-atoms,
n is an integer from 1 to 5000,
wherein the recurring units [(A)$_a$-(B)$_b$-(C)$_c$] can be identical or different.

4. A compound according to claim 3, wherein
R¹ to R⁸ are independently of each other H;
halogen;
straight chain, branched or cyclic alkyl with 1 to 20 C-atoms, which is unsubstituted, mono- or poly-substituted by F, Cl, Br, I or CN, and in which one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH═CH— or —C≡C— in such a manner that O and/or S atoms are not linked directly to one another; or
a mono-, bi- or tricyclic aromatic or heteroaromatic group with up to 25 C atoms that is optionally substituted with one or more groups selected from H, halogen and straight chain, branched or cyclic alkyl with 1 to 20 C-atoms, which is unsubstituted, mono- or poly-substituted by F, Cl, Br, I or CN, and in which one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH═CH— or —C≡C— in such a manner that O and/or S atoms are not linked directly to one another.

5. A compound according to claim 1, wherein n is an integer from 2 to 5000.

6. A compound according to claim 3, wherein n is an integer from 2 to 5000.

7. A compound according to claim 3, wherein R¹, R³, R⁴, R⁵, R⁷ and R⁸ are selected from H, $C_1$–$C_{20}$-alkyl, $C_1$–$C_{20}$-alkyl substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, optionally substituted aryl, or optionally substituted heteroaryl.

8. A compound according to claim 6, wherein R¹, R³, R⁴, R⁵, R⁷ and R⁸ are selected from H, $C_1$–$C_{20}$-alkyl, $C_1$–$C_{20}$-alkyl substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, optionally substituted aryl, or optionally substituted heteroaryl.

9. A compound according to claim 3, wherein R² and R⁶ are each selected from $C_1$–$C_{20}$-alkyl, $C_1$–$C_{20}$-alkyl substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, optionally substituted aryl, or optionally substituted heteroaryl.

10. A compound according to claim 6, wherein R² and R⁶ are each selected from $C_1$–$C_{20}$-alkyl, $C_1$–$C_{20}$-alkyl substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, optionally substituted aryl, or optionally substituted heteroaryl.

11. A compound according to claim 7, wherein R² and R⁶ are each selected from $C_1$–$C_{20}$-alkyl, $C_1$–$C_{20}$-alkyl substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, optionally substituted aryl, or optionally substituted heteroaryl.

12. A compound according to claim 8, wherein R² and R⁶ are each selected from $C_1$–$C_{20}$-alkyl, $C_1$–$C_{20}$-alkyl substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, optionally substituted aryl, or optionally substituted heteroaryl.

13. A compound according to claim 3, wherein said compound is selected from the following formulae

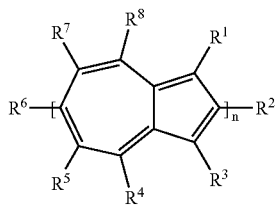
Ib
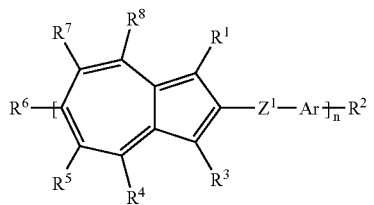
Id
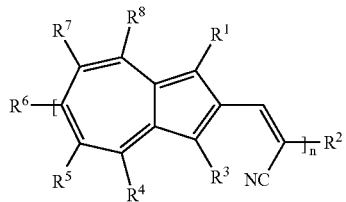
If
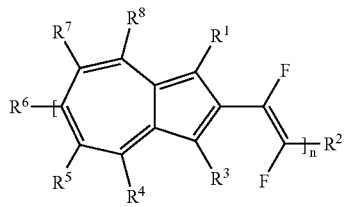
Ig
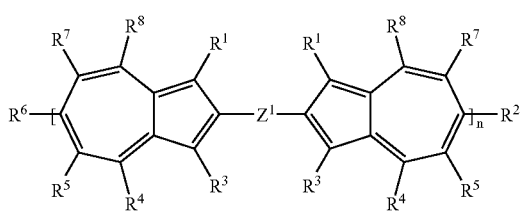
Ih
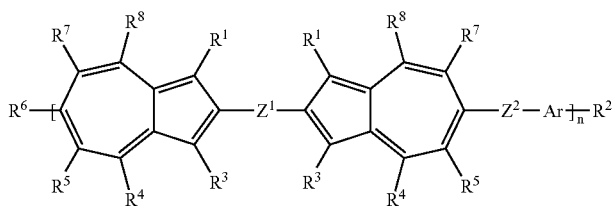
Ii
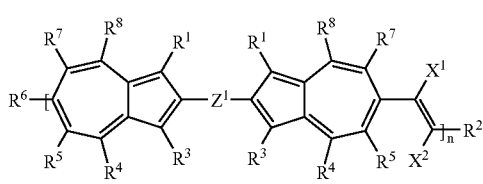
Ik
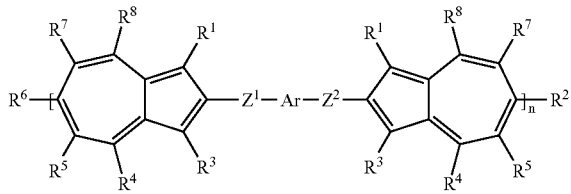

-continued
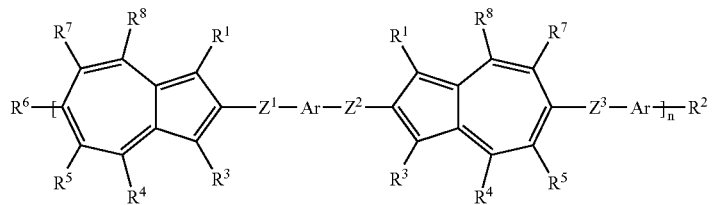
Im
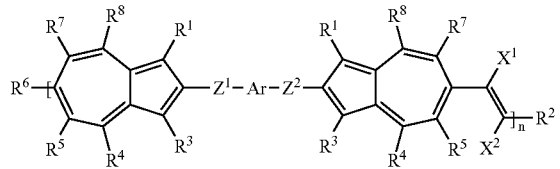
In
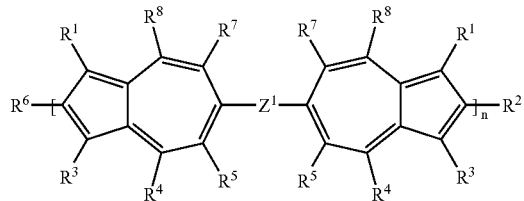
Io
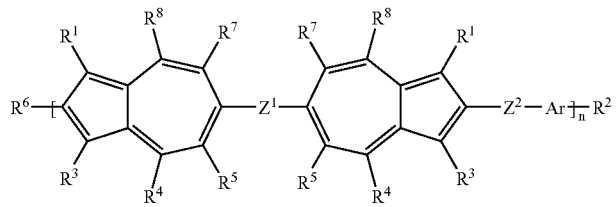
Ip
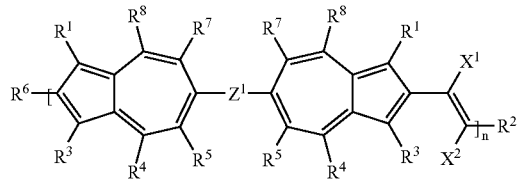
Iq
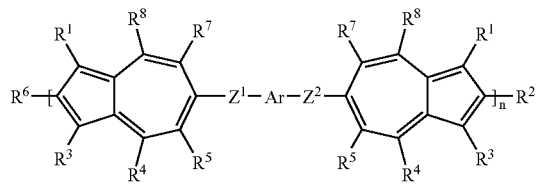
Ir
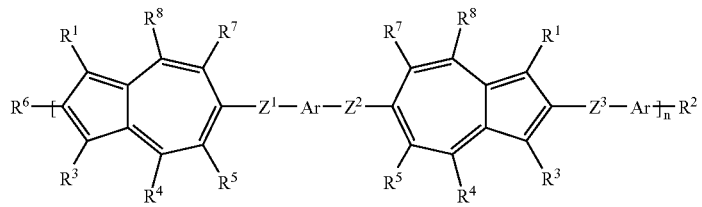
Is -continued
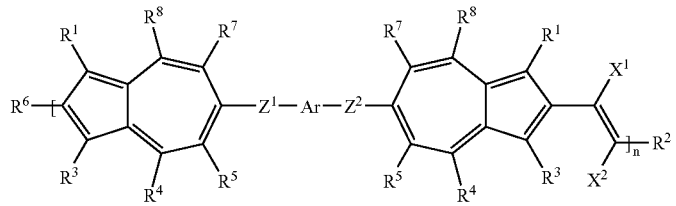
wherein
Ar is $(ar)_m$,
ar is arylene or heteroarylene,
m is 1, 2 or 3, and
$Z^1$, $Z^2$ and $Z^3$ are independently of each other $-CX^1=CX^2-$, $C\equiv C-$ or a single bond.
14. A compound according to claim 1, wherein said compound is oxidatively or reductively doped to form conducting ionic species.
* * * * *

UNITED STATES PATENT AND TRADEMARK OFFICE
CERTIFICATE OF CORRECTION

| | | |
|---|---|---|
| PATENT NO. | : 7,034,174 B2 | Page 1 of 1 |
| APPLICATION NO. | : 10/314939 | |
| DATED | : April 25, 2006 | |
| INVENTOR(S) | : Louise Farrand et al. | |

It is certified that error appears in the above-identified patent and that said Letters Patent is hereby corrected as shown below:

Column 15, line 55, reads "compound comprising" should read -- compound having --

Column 16, line 11-12, reads "comprises at least two" should read -- comprises more than two --

Column 16, line 12, reads "or at least" should read -- or more than --

Column 16, line 39, reads "thereof." should read -- thereof; wherein $R^0$ and $R^{00}$ are independently of each other H or alkyl with 1 to 12 C atoms. --

Column 18, line 9, reads "to claim 1," should read -- to claim 3, --

Column 19, insert --Ia-- to the right of the first compound

Column 19, insert --Ic-- to the right of the second compound

Column 19, insert --Ie-- to the right of the third compound

Signed and Sealed this
Twenty-eighth Day of December, 2010

David J. Kappos
*Director of the United States Patent and Trademark Office*